US006280788B1

(12) United States Patent
Rakhorst et al.

(10) Patent No.: US 6,280,788 B1
(45) Date of Patent: *Aug. 28, 2001

(54) METHOD AND A SYSTEM FOR MANUFACTURING A CATHETER AND A CATHETER MANUFACTURED BY THAT METHOD

(75) Inventors: Gerhard Rakhorst, Groningen; Gijsbertus Jacob Verkerke, Haren, both of (NL); Günter Brinckmann, Wilhelmshaven (DE)

(73) Assignee: Rijksuniversiteit Groningen (NL)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/077,117
(22) PCT Filed: Nov. 22, 1995
(86) PCT No.: PCT/NL95/00399
 § 371 Date: Aug. 26, 1998
 § 102(e) Date: Aug. 26, 1998
(87) PCT Pub. No.: WO97/18936
 PCT Pub. Date: May 29, 1997

(51) Int. Cl.$^7$ ........................................... A61L 2/00
(52) U.S. Cl. .................. 427/2.1; 427/430.1; 604/524; 604/264
(58) Field of Search ...................... 427/2.1, 2.24, 427/358, 430.1; 118/404, 407, DIG. 11; 604/523, 524, 526, 527, 533, 534, 535, 539, 264

(56) References Cited

U.S. PATENT DOCUMENTS

| 610,224 | * | 9/1898 | Braddock . | |
|---|---|---|---|---|
| 813,618 | * | 2/1906 | Chapman et al. . | |
| 2,127,413 | * | 8/1938 | Leguillon . | |
| 3,557,749 | * | 1/1971 | Farago . | |
| 3,638,919 | * | 2/1972 | Phipps | 366/262 |
| 3,842,799 | * | 10/1974 | Podkletnov | 118/408 |
| 3,930,462 | * | 1/1976 | Day . | |
| 4,024,046 | * | 5/1977 | Lupinski et al. | 204/624 |
| 4,259,379 | * | 3/1981 | Britton et al. | 427/356 |
| 4,993,354 | * | 2/1991 | Makita et al. | 118/407 |
| 5,009,933 | * | 4/1991 | Matsuda et al. | 427/287 |
| 5,217,533 | * | 6/1993 | Hay et al. | 118/63 |

* cited by examiner

Primary Examiner—Richard K. Seidel
Assistant Examiner—Jeremy Thissell
(74) Attorney, Agent, or Firm—Michaelson & Wallace; Peter L. Michaelson; Edward M. Fink

(57) ABSTRACT

For manufacturing a catheter tubing (50), a container (1, 21) provided with a passage (15, 35, 36), a mandrel (7) sealing off that passage (15, 35, 36) when inserted into said passage and a solution (14) containing a dissolved plastic in the container (1, 21) up to a level above the passage (15, 35, 36) are provided. Repeatedly, the mandrel (7) is inserted into the passage and at least a section of the mandrel (7) is passed through the passage (15, 35, 36) and the solution (14) in an upward direction. When sufficient plastic material has adhered to the mandrel (7), the catheter tubing (50) is removed from the mandrel (7). Thus, catheters having thin, smooth walls of a uniform thickness can be manufactured without expensive machinery and tools. A system for carrying out the method and particular catheters obtainable by that method are also described.

6 Claims, 5 Drawing Sheets

METHOD AND A SYSTEM FOR MANUFACTURING A CATHETER AND A CATHETER MANUFACTURED BY THAT METHOD

FIELD AND BACKGROUND OF THE INVENTION

The invention relates to a method and a system for manufacturing a catheter and to a catheter manufactured by that method.

Known methods of manufacturing catheter tubing are extrusion and dipping. Advantages of the extrusion process are that it is well-controlled and provides a catheter tubing with a smooth thin wall of a very constant thickness. However, extrusion requires relatively expensive machinery end tools. Therefore, it is mainly suitable for the production of substantial lengths of catheter tubing having a uniform cross-section, To manufacture a catheter, the catheter tubing has to be cut to the required length(s) and fittings have to be connected to the tubing. To avoid blood damage when the catheter is brought in contact with a patient's blood in-vivo, special adhesives have to be used and smooth transitions at the fittings are required. Furthermore, catheters generally comprise reinforcement material which is uncovered when the catheter is cut to the required length. Special measures are required to cover the reinforcement material to avoid contact between a patient's blood and the reinforcement material.

In UK patent application 2 187 670 it is described to manufacture a catheter having a funnel portion of rubber or other suitable material by placing the funnel over a former and dipping the catheter with the former one or more times in a latex solution.

However, dipping has been found difficult to control and did not provide satisfactory results, as is described in "Transarterial Blood Pumps, Feasibility Phase, Final Report"; Authors: H. Duffor at al.; Ed.: Dr Or G. J. Verkerke and Dr G. Rakhorst—Groningen ISBN 90-74280-02-1.

Furthermore, a particular requirement of catheters to be brought in direct contact with a patient's blood is that the ends and transitions at fittings are as smooth as possible and that all surfaces to be contacted with blood consist exclusively of biocompatible materials which cause as little damage as possible to the blood.

SUMMARY OF THE INVENTION

One object of the invention is to provide a method of manufacturing a catheter efficiently on a small scale without expensive machinery or tools, so that catheters can efficiently be manufactured in a great variety, and with which catheters with smooth, thin walls of uniform thickness can be obtained.

Another object of the invention is to provide a low-cost system with which catheters can be manufactured efficiently at small scale in a great variety of lengths and shapes, and with which catheters with smooth, thin walls of uniform thickness can be manufactured.

Yet another object of the invention is to provide catheters which are particularly smooth at the ends or in the area of fittings to reduce blood damage to a minimum.

According to the present invention, catheters having smooth thin walls of constant thickness can efficiently be manufactured on a small scale without expensive machinery or tooling by a method in which use is made of a container with at least one passage in a lower part thereof, a mandrel sealing off this passage when inserted therein and a solution containing a plastic in the container, a cycle of inserting the mandrel into the passage and moving at least a section of the mandrel through the passage and the solution in an upward direction is repeatedly carried out to form a catheter tubing on said section of the mandrel, and the catheter tubing formed on the mandrel is removed from the mandrel.

As in a dipping method, the thickness and the distribution of the plastic material over the mandrel depends on the viscosity of the solution, the gravity and the velocity at which the mandrel is pulled out of the solution. However, since consecutive sections of the mandrel enter the solution from below and leave the solution in upward direction, a uniform residence time in the solution of at least a substantial part of the mandrel during each cycle can easily be obtained by passing that part of the mandrel through the solution with a constant velocity. Thus, the extent to which plastic adhered to the mandrel is affected by the solvent during immersion in the solution is uniformly distributed over the part of the mandrel passed through the solution at a constant velocity. This results in a well-controlled uniform thickness of each layer. A multitude of these layers applied consecutively forms a catheter tubing constituted by a plurality of very thin layers and having a uniform thickness. Since the mandrel may be held vertically, no particular measures for avoiding bending of the mandrel are required.

If a predetermined variation of the residence time over the length of the mandrel is desired, the velocity of the mandrel can be varied accordingly.

In accordance with a further aspect of the invention, a system specifically adapted for carrying out the method according to the invention is provided, which system includes a container with a cavity for holding a solution containing a dissolved plastic material, which container is provided with at least one passage in a lower part of the cavity, a mandrel sealing off that passage when inserted into that passage, and means for passing at least a section of said mandrel through said passage in an upward direction.

The invention can further be embodied in a catheter which can specifically be obtained by a particular mode of carrying out the method according to the invention. Such a catheter according to the present invention includes a tubing and a fitting, the fitting being encapsulated by wall material of the tubing extending along the inside and the outside of said fitting.

Such a catheter can for example be manufactured by positioning the fitting over a wall coating previously applied to the mandrel and by subsequently applying the further layer or layers of wall material.

When the catheter is finished, a continuation of the wall material of the tubing of the catheter encapsulates at least parts of the fitting, so that a very smooth seamless outer surface is obtained in the area of the fitting. Any adhesive between the wall material and the fitting is shielded from blood and tissue of the patient, when the catheter extends into a patient.

Further details and advantages of the method, the system and the catheter according to the present invention appear from the following description, the drawings and the claims.

MODES FOR CARRYING OUT THE INVENTION

Figure 1:
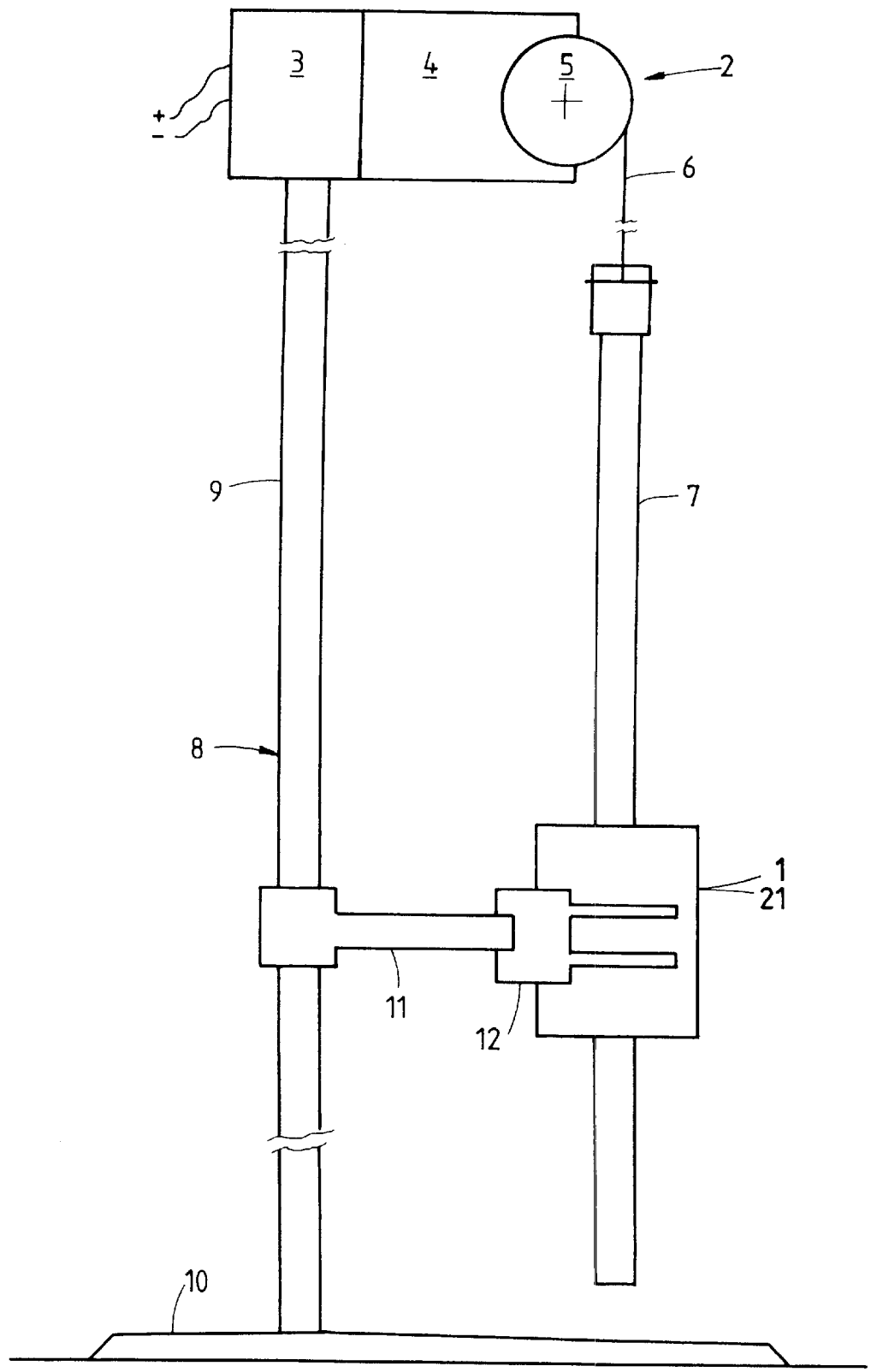
FIG. 1 is a schematic representation of a system according to the invention for carrying out the method according to the invention.

In FIG. 1 a system according a presently most preferred embodiment of the invention for manufacturing a catheter is schematically shown.

The system is composed of a container or receptacle 1, 21, a lifting assembly 2 arranged above that container 1, 21 and a mandrel 7. The lifting assembly consists of a motor 3, a gear box 4, a spool 5 and a cord or string 6 from which the mandrel is detachably suspended.

To position the container 1, 21 and the lifting assembly 2 in the desired configuration, the container 1, 21 and the lifting assembly 2 are mounted on a support structure 8, composed of a vertical column 9, a foot 10 and an arm 11 whose position along the column 9 is adjustable. The arm 11 is provided with a clamp 12 for holding the container 1, 21.

Containers 1, 21 for use in the system shown in FIG. 1 are shown in more detail in FIGS. 2, 4, 5 and 6. The containers 1, 21 are provided with a cavity 13, 33 for holding a solution 14, 34 containing a dissolved plastic material. Furthermore, the containers 1, 21 are each provided with at least one passage 15, 35, 36 spaced from the top of the cavity 13, 33. Preferably, the passages 15, 35, 36 are provided in the bottom of the containers 1, 21 to allow passage of the mandrel 7 therethrough in a vertical direction.

The mandrel 7 and the opening 15 or openings 35, 36 have cross-sections adapted to allow passage of the mandrel 7 through the passage 15 or passages 35, 36 and to ideal off the passage 15 or passages 35, 36 while the mandrel 7 extends therethrough.

By the lifting assembly 2, the mandrel 7 or at least a section of the mandrel 7 can be passed in upward direction through the passage 15 or passages 35, 36.

Figure 2:
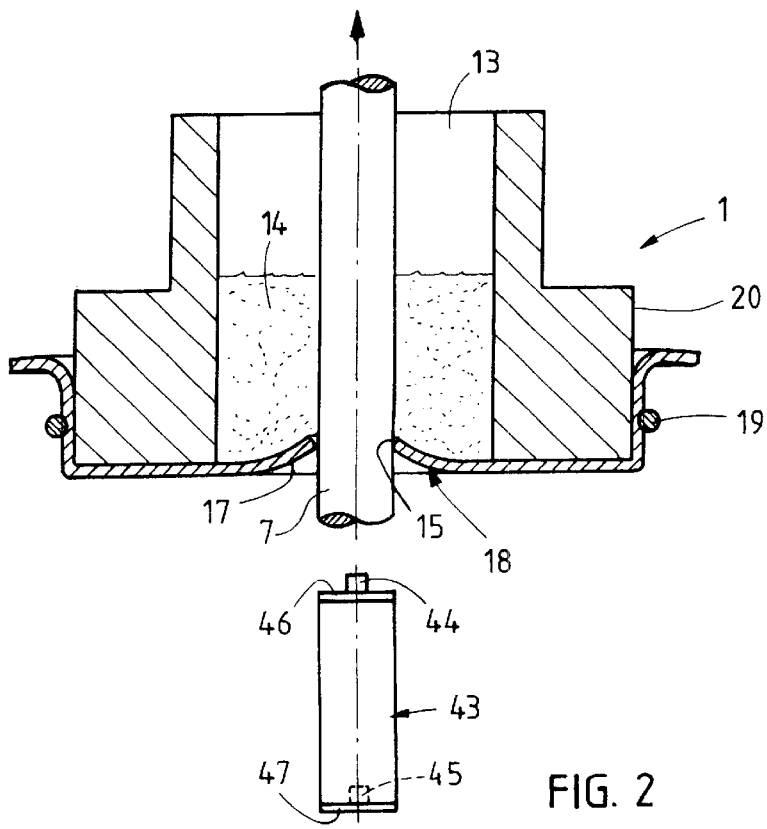
FIG. 2 is a side view in cross section of a container for use in the system shown in FIG. 1.

Manufacturing a catheter tubing using the system shown in FIG. 1 with the container shown in FIG. 2 is started by inserting the mandrel 7 into the opening 15 so that the opening 15 is sealed and connecting the mandrel 7 to the cord 6 of the lifting assembly 2. Then the solution 14 containing a dissolved plastic is fed into the container 1 up to a level above the passage 15. Then, a section of the mandrel 7 is moved through the passage 15 and the solution 14 in an upward direction by energizing the motor 3.

The mandrel 7 can be lifted until it leaves the opening 15. The solution flowing away through the opening can be caught in a receptacle provided under the opening. It is also possible to remove the solution 14 just before the mandrel 7 is pulled out of the opening 15. A third possibility is to provide at least one plug 43 or other mandrel (see FIG. 2) of essentially the same cross section as the mandrel 7 and adapted to be in sealing contact with, alternately, the leading and the trailing end of a mandrel 7. Such a plug or other mandrel seals off the opening when the mandrel 7 has passed the opening until the next mandrel, yet another mandrel or again the same mandrel 7 is inserted into the opening 15. Thus, the solution 14 can also be held in the cavity 13 after the mandrel 7 has left the opening 15. The solution only has to be replenished to replace solution which has adhered to the mandrel or mandrels. Some additional solvent may have to be replenished to replace evaporated solvent.

The plug 43 is provided with a projection 44 at its leading end and a recess 45 at is trailing end to allow concentric positioning with leading and trailing mandrels 7. Sealing rings 46, 47 at both the trailing and leading ends of the plug 43 are provided to avoid leaking between the plug and leading or trailing mandrels 7.

The steps of pulling the mandrel 7 through the opening 15 and the solution 14 and, if necessary, collecting solution drained through the opening 15 and refilling the cavity 13 each time the opening 15 is closed upon a next passage of the mandrel 7, are repeated until the layer of catheter tubing wall material adhered to the mandrel 7 has the required thickness.

To provide the solution in the container at the beginning of each drawing cycle, the mandrel 7 may each time be inserted into the passage 15 before the solution 14 is fed to the cavity 13.

However, if the passage is closed off between successive passages of the mandrel 7, e.g. by a plug or another mandrel as described above, it is not necessary to fend the solution 14 into the cavity 13 each time the mandrel 7 has ben inserted into the passage, because the solution 14 is always held in the cavity 13.

Draining of the solution via the passage 15 can also be avoided by providing a flap-shaped valve which closes off the passage 15 when no mandrel extends through the passage. Another possibility of avoiding draining of the solution via the passage 15 is to drain the solution via a draining channel communicating with the interior of the container just before the trailing end of each mandrel leaves the passage 15. The draining channel or another channel can be used for refilling the container each time a leading end of a mandrel has been inserted into the passage 15. The container can also be refilled by simply pouring the solution into the container from above.

Finally, the catheter tubing wall material adhered to the mandrel can be removed from the mandrel 7.

Figure 3:
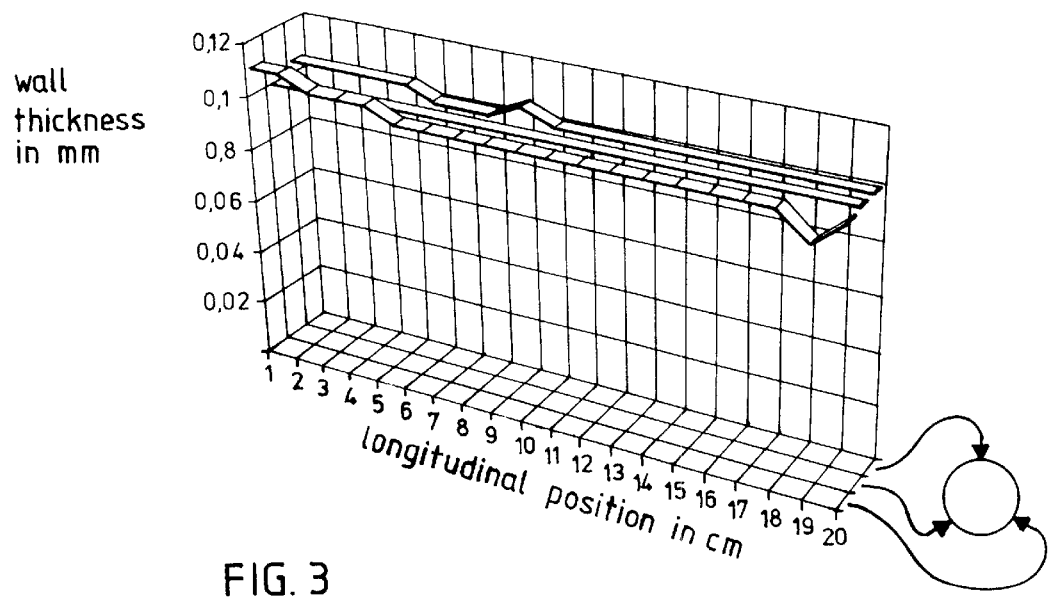
FIG. 3 is a graph showing a wall thickness distribution obtained with the method according to the invention.

FIG. 3 shows that a very even thickness distribution can be obtained. The results shown in FIG. 3 were obtained under the following conditions:

Mandrel: PTFE 400×8 mm

Drawing volocity: 3 mm/s

Concentration: 10%

Plastic: polyetherurethane (Pellethane 80 AE made by Dow)

Solvent: tetrahydrofuran

Number of draws: 6

Time between successive draws: 5 minutes

Temperature: room temperature

These results proved to be very well reproducible. The surface was smooth. No drops or air bubbles appeared in the adhered plastic. The catheter wall tubing formed around the mandrel was easily removable from the PTFE mandrel. In spite of the vertical orientation of the mandrel, the wall thickness showed no increase towards one end of the catheter due to wall material descending along the mandrel.

To easily accommodate the cross section of the opening to the increasing total thickness of the mandrel and the wall material adhered to tho mandrel 7, the passage 15 and the passages 35, 36 each have flexible edges 17, 37. In the preferred embodiment, this is achieved by providing the passages 15, 35, 36 in the form of holes in flexible (preferably latex) membranes 1a, 38. The membranes 18, 38 can be fixed by a clamping ring 19 extending around a container body 20 as is shown in Pig. 2. The size of the passage 15 is slightly smaller than the size of the mandrel and the form of the passage 15 corresponds to the form of the cross section of the mandrel 7 (in the present embodiment both have a circular shape). When the mandrel 7 is inserted into the passage 15, the edges of the passage 15 are slightly stretched so that the size of the passage 15 is increased to the size of the cross section of the mandrel 7 and any material applied to the mandrel 7.

Figure 7:
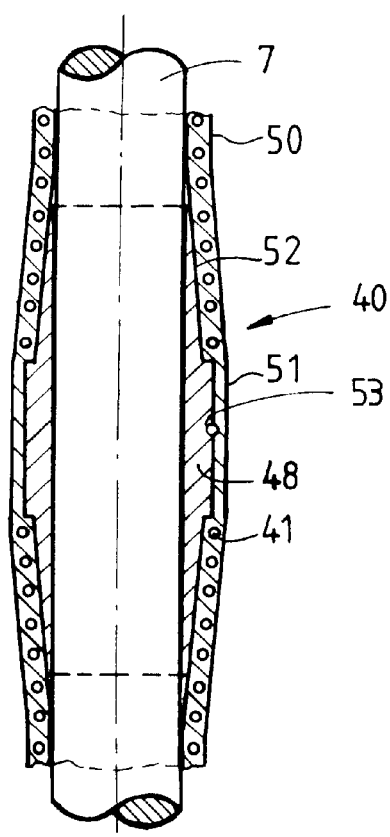
FIG. 7 is a schematic side view in cross section of a part of a catheter comprising a fitting positioned over a mandrel.
Figure 8:
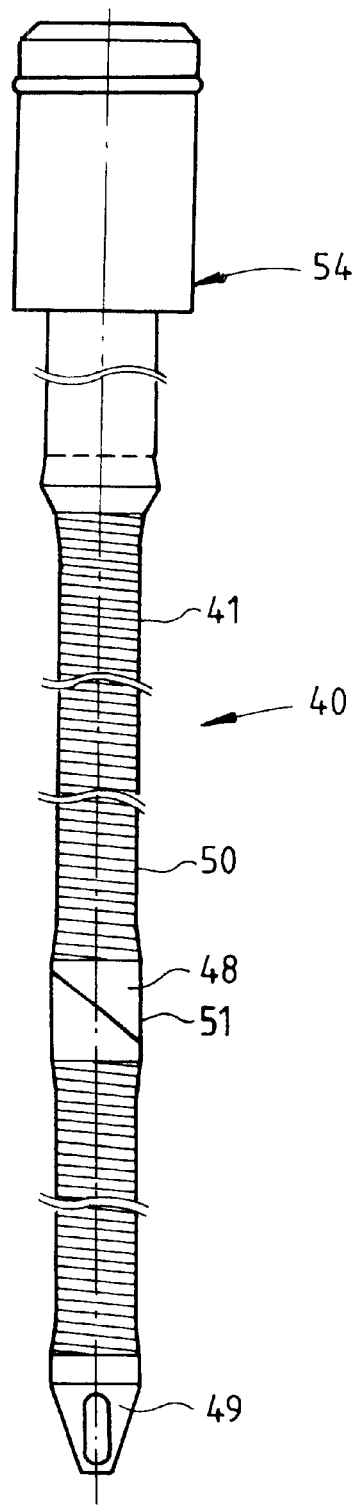
FIG. 8 is a side view of a catheter according to the invention.

In particular for large lumen catheters it is on the one hand desirable to have a wall which is as thin as possible to obtain a great inner lumen at an outer diameter which is as small as possible, while, on the other hand, the catheter must be able to withstand substantial over-pressure (generally at least about 95 kPa) and under-pressure (generally at least 60 kPa), To prevent the catheter from expanding or collapsing a reinforcement can be applied around the plastic layer adhered to the mandrel 7. Depending upon the required properties of the catheter, the reinforcement may for example be made of stainless steel wire, nylon or special high-modulus fibres such as carbon fibre or aramide embedded in epoxy resin. The material can for example be applied around the plastic layer adhered to the mandrel 7 in the form of a single or repeated spring, successive rings, a weave, a braid or longitudinal bars. The catheter 40 shown in FIGS. 7 and 8 is provided with a single coil 41 of stainless steel wire of a diameter of 0.12 mm with 2.4 windings per mm and showed both a good flexibility and the required resistance against over-pressure and under-pressure. Moreover, the reinforced catheter tubing proved easy to cut to the required length, because only one wire has to be cut.

To avoid direct contact between the reinforcement 41 and the patient's blood and to provide a smooth outer surface, the reinforcement has to be covered with an outer coat.

Figure 4:
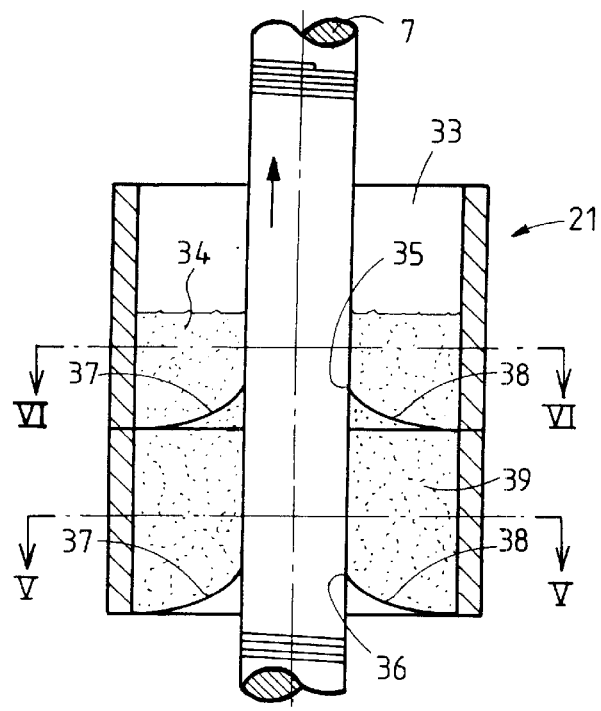
FIG. 4 is a side view in cross section of a second container for use in the system shown in FIG. 1 along the plane IV—IV in FIGS. 5 and 6.

According to the preferred mode of carrying out the method according to the invention, a container having two passages 35, 36, as shown in FIG. 4, is provided and an interspace 39 between these passages 35, 36 is also filled with the solution 14.

Figure 5:
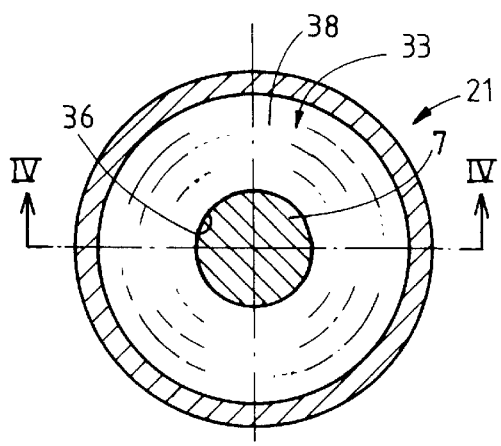
FIG. 5 is a top plan view in cross section along the line V—V in FIG. 4.
Figure 6:
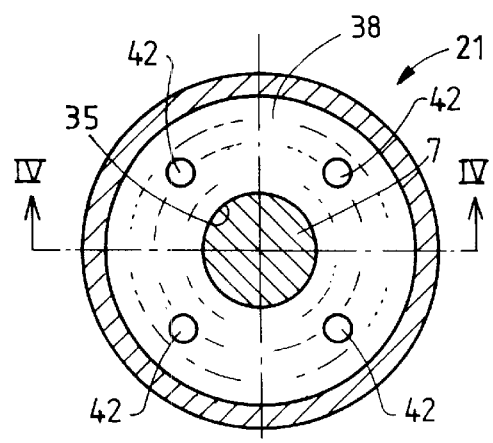
FIG. 6 is a top plan view in cross section along the line VI—VI in FIG. 4.

To this and the system is provided with a container 21 as shown in FIGS. 4, 5 and 6 having two passages 35, 36 in an axially spaced configuration and a chamber 39 between these passages 35, 36.

When the mandrel 7 is passed through the two passages 35, 36, the edges of the lower passage 36 essentially prevent fluid from leaking down along the mandrel 7. The edges of the upper passage 35 rake bubbles from the passing mandrel 7. In this manner, smooth, substantially bubble free further layers are obtained. A particular advantage of providing two or more of the passages 35, 36 is that leaking and entraining of bubbles can effectively be counteracted at a low contact pressure between the edges of the passages and the material passing through the passage, so that relative displacements of the windings of the reinforcements by the edges of the passages can be avoided. Such displacements would lead to an uneven distribution of the pitch between successive windings and thus a stiffness which varies along the length of the catheter.

To assure that the chamber 39 between the passages remains filled with solution, the cavity 33 of the container communicates with the chamber 39 via accommodating passages 42. In the present embodiment, these accommodating passages are provided in the form of holes 42 in the upper membrane 38.

Although the container according to FIGS. 4, 5 and 6 is particularly advantageous for applying material to an uneven basis, for example after reinforcements or fitting have been applied to the mandrel, it can of course also be used to apply plastic material to an even basis, such as directly to the mandrel. The same containers can thus be used for applying the plastic material before and after reinforcements have been applied.

The material encapsulating the reinforcement can advantageously be applied under the same conditions as described above with respect to the layers applied before the reinforcement was applied, except that preferably a container as shown in FIGS. 4, 5 and 6 is used. Particularly good results have been obtained with the use of a polyesterurethane (Estane 74 D from B.F. Goodrich). This material is somewhat stiffer than Pellethane 80 AE, which may also be advantageous for the layers applied before the reinforcement is applied.

A particular advantage of the system and the method according to the present invention is that catheters with a great variety of integrated fittings can efficiently be manufactured. Moreover, the catheters can even be tailor-made with fittings exactly in positions specified for particular patients and clinical applications.

According to the preferred mode, first an inner coat is applied to the mandrel 7, whereafter the inner coat is cut to sections of the required lengths. Some sections of inner coat are removed from the mandrel 7. Then fittings 48, 49 and removed sections of inner coat are positioned onto the mandrel, cone shaped sockets 52 of the fittings 48, 49 are urged under ends of the inner coat sections and preferably bonded to the inner coat ends by an adhesive. Then the reinforcement is applied over the inner coat and the fittings 48, 49, a wider pitch between successive windings being formed where the windings extend directly along the outside of the fittings 48, 49. Finally, the assembly thus obtained is again drawn through the solution 14 as described again until the required outer coat encapsulating the reinforcement and at least parts of the fittings 48, 49 has been obtained.

The fitting 48 is provided with a helical groove 53 receiving a winding of the reinforcement extending along the outside of a central part of the fitting 48, so that the helical projecting edge formed by this winding is avoided, or at least reduced in size, and additional axial fixation of the fitting 48 is obtained.

By positioning the fittings 48, 49 over the mandrel 7 between two of the cycles in each of which cycles the mandrel 7 is drawn through the solution 14, a catheter 40 with fittings 48, 49 completely or partially encapsulated by wall material of the tubing 50 of the catheter is obtained. More specifically, the seam between wall material applied before the fitting was mounted and material of the fitting is also encapsulated by wall material of the cathoter tubing. This results in a very smooth outer surface. Furthermore, any adhesive in the seam is encapsulatod by wall material and thus shielded from blood and tissue of the patient when the catheter is in use extending into a patient.

Thus, for example a catheter 40 as shown in FIGS. 7 and 8 can be obtained which catheter 40 comprises a tubing 50 and a fitting 48 encapsulated by wall material 51 of the tubing 50. The wall material 51 encapsulating the fitting 48 has a stepped thickness at the ends of the parts of wall material applied to the mandrel 7 before the fitting 48 was positioned onto the mandrel 7, as a result of which the step at the proximal end of each socket is smoothed.

By applying the reinforcement 41 after the fittings 48, 49 have been positioned onto the mandrel 7, the reinforcement also extends around parts of the fittings 48, 49. The reinforcement wound around the fitting provides a particularly reliable integration of the fittings 48, 49 in the catheter 40.

At the fitting 48, which is positioned between ends of the catheter 40, the wall material 51 of the tubing 50 enveloping the fitting 48 forms a continuation in longitudinal direction of wall material of the tubing 50, bridging wall material of the tubing on one side of the fitting 48 and wall material of the tubing at the opposite side of the fitting 48. Thus, the outer coat only has to be interrupted at the fitting 49 where this is required for providing a passage to the inside of the fitting 48. The fitting 48 may for example be provided in the form of a valve structure.

To de-aerate the catheter 40, the catheter has to be closed off outside the patient's body. To this end, the distal end (the end opposite the fitting 49) of the catheter 40 is provided with a connector 54. The connector 54 is attached to the catheter tubing 50 without forming a narrowed inside cross section and may for example be connected to a connector of a heart pump.

Figure 9:
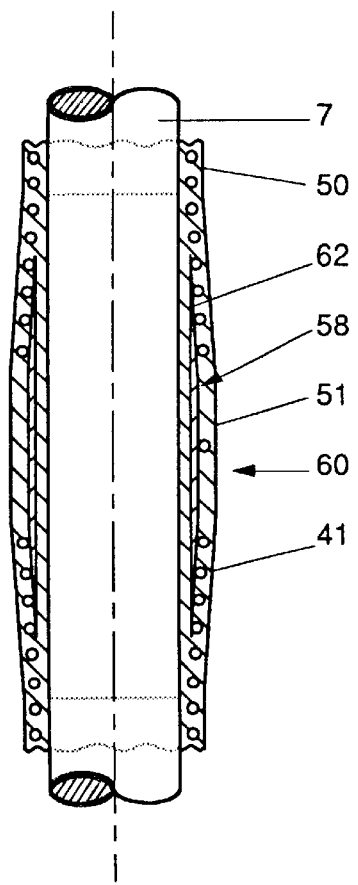
FIG. 9 is a schematic side view in cross section of a part of a catheter according to the invention comprising a fitting positioned over a mandrel.

In FIG. 9 a section of a catheter 60 is shown which is manufactured in a slightly different manner. The fitting 58 is positioned over plastic material applied to the mandrel 7 during previous passages of the mandrel 7 through the solution 14. Then the reinforcement is applied over the inner coat and the fittings as in the example described hereinbefore. In this example the pitch of the windings 41 of the coil is maintained the same where the windings are wound around sockets 62 of the fitting 58. A wider pitch is provided where the windings extend along a central part of the fitting 58 to obtain an interspace sufficiently large for a passage interconnecting the inside and the outside of the catheter 60. Finally, as in the example described hereinbefore, the assembly thus obtained is again drawn through the solution 14 until the required outer coat encapsulating the reinforcement and at least parts of the fitting 58 has been formed.

By positioning the fitting 58 over plastic layers applied to the mandrel 7 during previous passages of the mandrel 7 through the solution 14 and by passing the mandrel 7 through the solution 14 after the fitting 58 has been positioned onto the mandrel 7, a catheter 60 with a fittings 58 completely or partially encapsulated by wall material of the tubing 50 of the catheter on its inside and its outside is obtained. The catheter 60 has no seams between wall material of the tubing 50 and material of the fitting 58. Instead, the fitting 58 is encapsulated by continuous layers of wall material of the catheter tubing. This results in a very smooth inner and outer surface. because the fitting is encapsulated between continuous inner and outer layers of wall material of the tubing 50, the integrity of the catheter is substantially improved. Especially the resistance against delamination between the fitting 58 and wall material of the tubing 50 when a portion of the catheter 60 adjacent the fitting 58 is bent sharply is substantially increased.

Fittings for a catheter often comprise a passage allowing communication between the inside of the catheter and the outside of the catheter. To provide passages through wall material of the catheter after the fitting 58 has been positioned and the formation of wall material has been completed, the wall material can be cut away where the passages are required.

Figure 10:
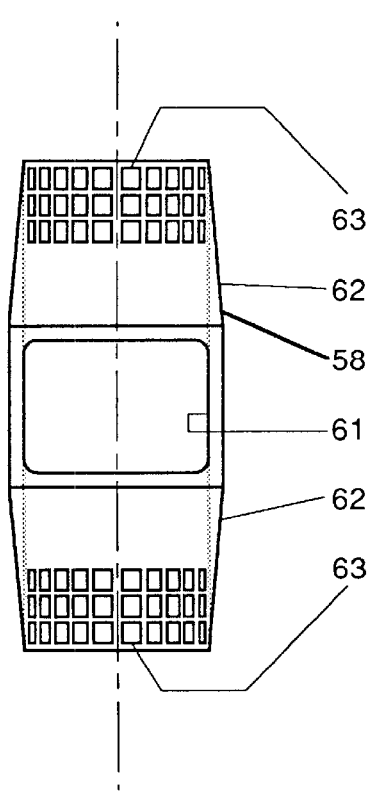
FIG. 10 is a side view of the fitting of the catheter shown in FIG. 9.

As appears from FIG. 10, the fitting 58 is provided with a central opening 61 into which a valve-unit can be mounted.

The sockets 62 of the fitting 58 are provided with openings 63. When plastic material is applied after the fitting 58 has been brought in position, plastic material fills up the openings and forms anchors between plastic material on the inside and the outside of the sockets 62. Thus the structural integrity between the fitting 58 and the wall material of the tubing 50 is further increased. Dependent on the design of the sockets and the plastic material used, the openings 63 can also be of a different design and be provided in different patterns.

What is claimed is:

1. A method of manufacturing a catheter (40) comprising the steps of:

providing a container (1, 21) provided with at least one passage (15, 35, 36);

providing a mandrel (7) sealing off said passage or passages (15, 35, 36) when inserted into said passage or passages (15, 35, 36);

providing a solution (14) containing a dissolved plastic in said container (1, 21) up to a level above said passage or passages (15, 35, 36);

forming a catheter tubing on the mandrel (7) by repeatedly carrying out a cycle of:
a. inserting said mandrel (7) into said passage or passages (15, 35, 36); and
b. moving at least a section of said mandrel (7) through said passage or passages (15, 35, 36) and said solution (14) in an upward direction; and removing the catheter tubing (50) formed on said mandrel (7) from said mandrel (7).

2. A method according to claim 1, wherein at least two of said passages (35, 36) are provided and ai interspace (39) between said passages (35, 36) is filled with said solution (14).

3. A method according to claim 1, wherein between two of said cycles a fitting (48, 49, 58) is positioned onto said mandrel (7).

4. A method according to claim 3, wherein a cone-shaped socket of the fitting (48, 49) is urged in-between a section of the mandrel (7) and plastic material applied to that section of the mandrel (7) during previous passages of that section through the solution (14).

5. A method according to claim 3, wherein the fitting (58) is positioned over plastic material applied to that section of the mandrel (7) during previous passages of that section through the solution (14).

6. A method according to claim 3, wherein, between two of said cycles, a reinforcement (41) is applied to layers formed on the mandrel (7) after the fitting (48, 49, 58) has been positioned onto said mandrel (7).

* * * * *